(12) United States Patent
Craig

(10) Patent No.: US 10,707,022 B2
(45) Date of Patent: Jul. 7, 2020

(54) FEEDTHROUGH CAPACITOR ASSEMBLY AND METHOD OF CLAMPING SAME TO A CONDUCTIVE SUBSTRATE

(71) Applicant: TE CONNECTIVITY CORPORATION, Berwyn, PA (US)

(72) Inventor: Evan Lawrence Craig, Vernon Hills, IL (US)

(73) Assignee: TE CONNECTIVITY CORPORATION, Berwyn, PA (US)

( * ) Notice: Subject to any disclaimer, the term of this patent is extended or adjusted under 35 U.S.C. 154(b) by 303 days.

(21) Appl. No.: 15/863,244

(22) Filed: Jan. 5, 2018

(65) Prior Publication Data
US 2019/0214198 A1 Jul. 11, 2019

(51) Int. Cl.
| | | |
|---|---|---|
| H01G 4/35 | (2006.01) | |
| A61N 1/375 | (2006.01) | |
| B25B 5/02 | (2006.01) | |
| B25B 5/10 | (2006.01) | |

(52) U.S. Cl.
CPC .............. *H01G 4/35* (2013.01); *A61N 1/3754* (2013.01); *B25B 5/02* (2013.01); *B25B 5/10* (2013.01)

(58) Field of Classification Search
CPC ............... H01G 4/35; H01G 4/32; H01G 2/02
See application file for complete search history.

(56) References Cited

U.S. PATENT DOCUMENTS

| | | |
|---|---|---|
| 7,725,177 B2 | 5/2010 | Iyer |
| 2005/0190527 A1 | 9/2005 | Stevenson et al. |

FOREIGN PATENT DOCUMENTS

| | | |
|---|---|---|
| EP | 2 258 442 A1 | 12/2010 |
| JP | 2739822 B2 * | 4/1998 |

OTHER PUBLICATIONS

International Search Report, International Application No. PCT/IB2018/059682, International Filing Date, Dec. 5, 2018.

* cited by examiner

*Primary Examiner* — Eric W Thomas

(57) ABSTRACT

A feedthrough capacitor assembly including a film-wound feedthrough capacitor and a mounting structure insulatively carrying the capacitor, the structure extendable through an opening in a conductive substrate and removably securable to the substrate. In response to opposed ends of the mounting structure applying a clamping force for non-movingly securing the capacitor to the substrate, the capacitor is not subjected to at least a portion of the clamping force.

17 Claims, 3 Drawing Sheets

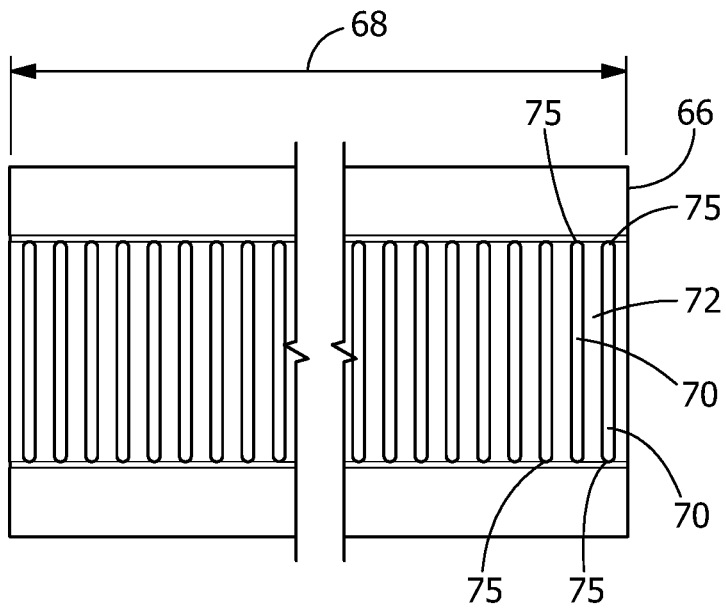
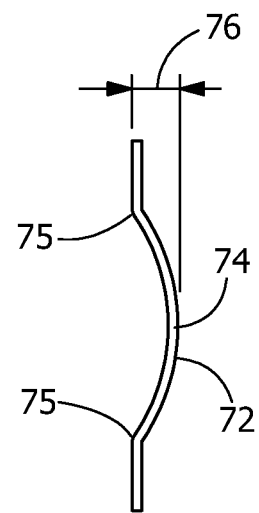
FIG. 4  FIG. 5
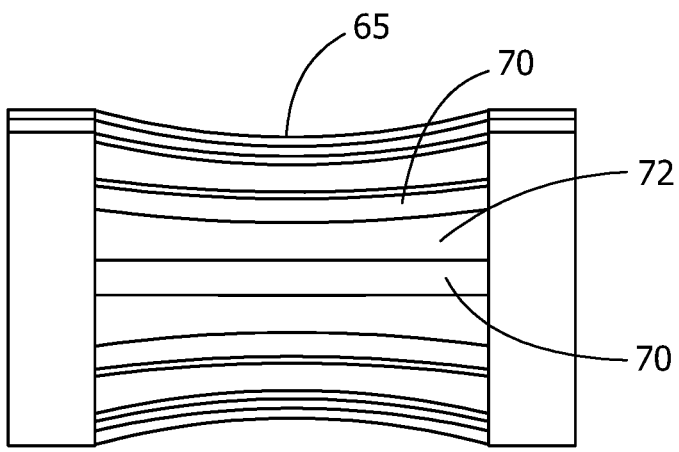
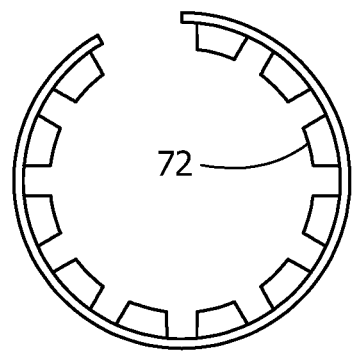
FIG. 6  FIG. 7

FEEDTHROUGH CAPACITOR ASSEMBLY AND METHOD OF CLAMPING SAME TO A CONDUCTIVE SUBSTRATE

FIELD OF THE INVENTION

The present invention is directed to feedthrough capacitor assemblies and method for clamping same to conductive substrates.

BACKGROUND OF THE INVENTION

Feedthrough capacitors are utilized in many electrical installations and equipment to suppress electromagnetic interference ("EMI"). However, there are challenges associated with the use of feedthrough capacitors in high current applications. More specifically, the large feedthrough conductors required for high current applications may be subjected to inertial forces exceeding the friction available from the clamping force, which clamping force being limited by the compressive strength of the feedthrough capacitor. In order to increase the compressive strength of the feedthrough capacitor, the capacitor requires an external enclosure and potting material. FIG. 1 shows a conventional feedthrough capacitor 10 including external enclosure 12 and potting material 14. Although some manufacturers have attempted to solder electrode washers to feedthrough capacitors, the thermal mass of the washers risk thermal damage to the feedthrough capacitors, and still require external enclosures and potting material.

Accordingly, there is a need for improved feedthrough capacitors that do not suffer from these drawbacks.

SUMMARY OF THE INVENTION

An embodiment is directed to a feedthrough capacitor assembly including a film-wound feedthrough capacitor and a mounting structure insulatively carrying the capacitor, the structure extendable through an opening in a conductive substrate and removably securable to the substrate. The capacitor includes a shaft having an axis and opposed enlarged ends, at least one of the opposed ends being removable from the shaft, at least one of the opposed ends being movable along the axis relative to another end, the shaft extendable through the substrate opening, The capacitor further includes a tubular conductive member received by the shaft, the conductive member extendable through the substrate opening. The capacitor assembly provides in response to insertion of the shaft and the member through the substrate opening and the opposed enlarged ends being sufficiently brought toward one another to an installed position, the opposed enlarged ends applying a first clamping force for nonmovingly securing the substrate to the conductive member. The capacitor is not subjected to at least a portion of the first clamping force.

A further embodiment is directed to a feedthrough capacitor assembly including a film-wound feedthrough capacitor and a mounting structure insulatively carrying the capacitor, the structure extendable through an opening in a conductive substrate and selectably securable to the substrate. The mounting structure includes a shaft having an axis and opposed enlarged ends, at least one of the opposed ends being removable from the shaft, at least one of the opposed ends being movable along the axis relative to another end, the shaft extendable through the substrate opening. The mounting structure further includes a tubular conductive member received by the shaft, the tubular conductive member extendable through the substrate opening. The capacitor assembly provides in response to insertion of the shaft and the tubular conductive member through the substrate opening and the opposed enlarged ends being sufficiently brought toward one another to an installed position, the opposed enlarged ends applying a first clamping force for securing the substrate to the tubular conductive member. The capacitor is not subjected to at least a portion of the first clamping force. The capacitor assembly provides a resilient member exerting a second clamping force independent of the first clamping force for securing the capacitor to the substrate.

A yet further embodiment is directed to a method of clamping a feedthrough capacitor to a conductive substrate, including securing a first electrical lead from an electrical source along a shaft of a mounting structure, the shaft having an axis and opposed enlarged ends, at least one of the opposed ends being removed from the shaft to receive the first electrical lead, at least one of the opposed ends being movable along the axis relative to another end, the shaft extendable through the substrate opening. The method further includes inserting the shaft through a tubular conductive member received by the shaft, the tubular conductive member insulatively extendable through the substrate opening, and inserting the shaft and the tubular conductive member through an opening in the conductive substrate. The method further includes inserting the tubular conductive member through the capacitor, and securing a second electrical lead associated with the electrical source along the shaft of the mounting structure. The method further includes securing the removed at least one opposed enlarged end to the shaft, and moving the opposed ends along the axis sufficiently toward one another to establish an installed position defining a first conductive path between the first electrical lead, the tubular conductive member and the second electrical lead, and a second conductive path between the first electrical lead, the tubular conductive member, the capacitor and the conductive substrate. The method further includes, upon establishing the installed position, the opposed enlarged ends apply a first clamping force for securing the substrate to the tubular conductive member, and the capacitor is not subjected to at least a portion of the first clamping force.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 4 is a plan view of an exemplary strip of material for constructing a conductive ring according to the present invention.

FIG. 5 is an end view of the strip of material of FIG. 4 according to the present invention.

FIG. 6 is an elevation of an exemplary conductive ring formed from the strip of material of FIG. 4 according to the present invention.

FIG. 7 is an end view of the conductive ring of FIG. 6 according to the present invention.

DETAILED DESCRIPTION OF THE INVENTION

The description of illustrative embodiments according to principles of the present invention is intended to be read in connection with the accompanying drawings, which are to be considered part of the entire written description. Terms such as "attached," "affixed," "connected," "coupled," "interconnected," "engaged," "installed" and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

Figure 1:
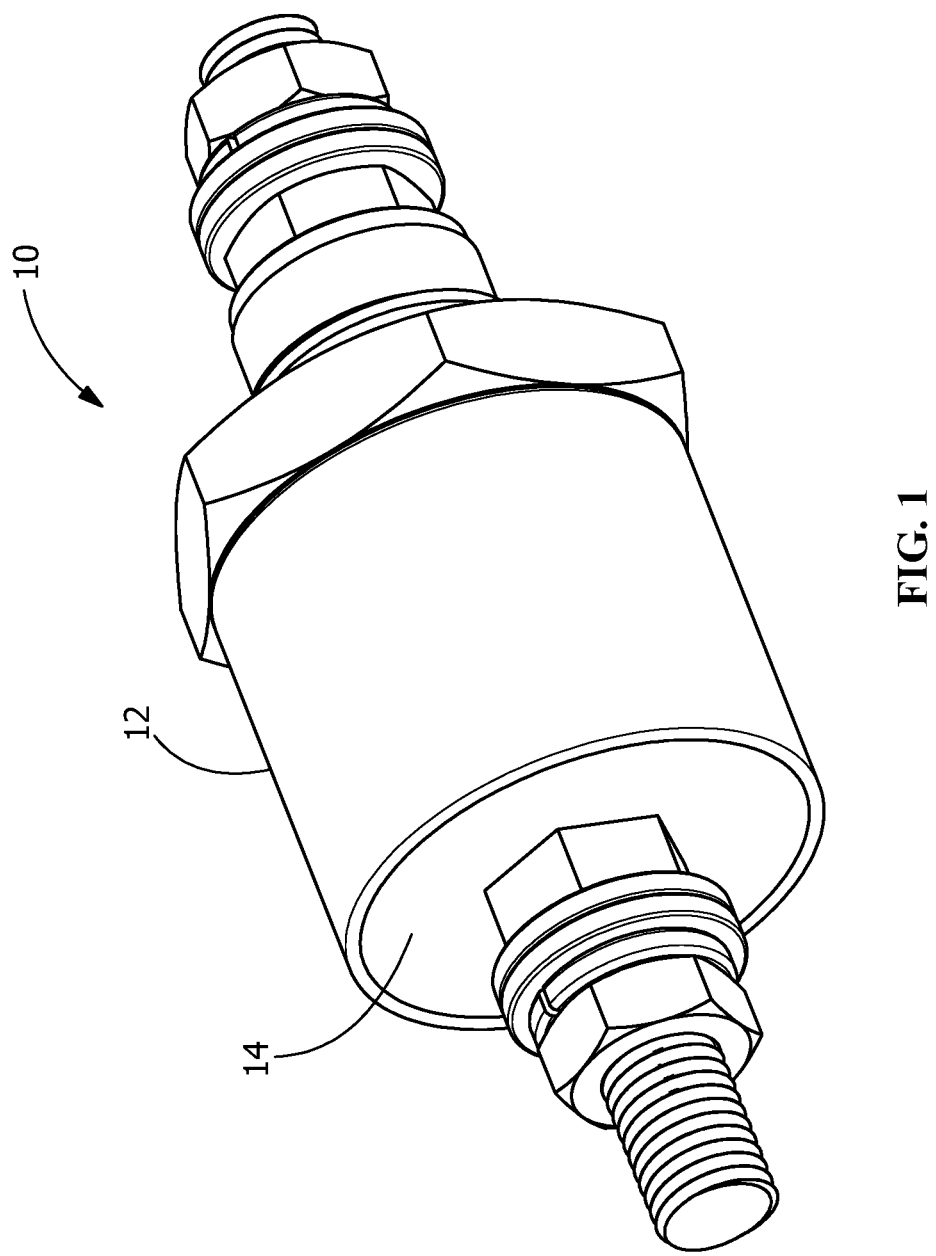
FIG. 1 is an upper perspective view of a prior art feedthrough capacitor.
Figure 2:
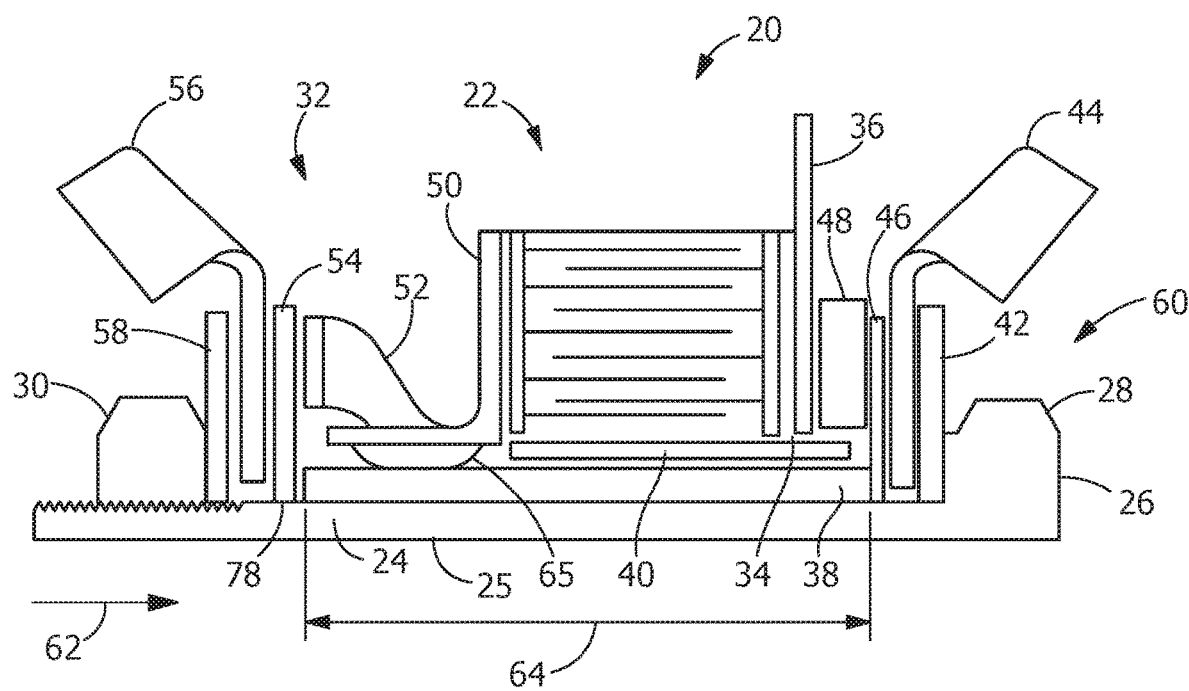
FIG. 2 is a cross section of an exemplary feedthrough capacitor assembly according to the present invention.

FIG. 2 is a cross section of an exemplary feedthrough capacitor assembly 20 of the present invention. Moreover, for purposes of clarity, only one half of the cross section is shown, as the other half of the cross section is essentially a mirror image positioned on the opposite side of a centerline axis or axis 25 of a shaft 24 of a mechanical fastener, such as a bolt 26. Bolt 26 has an enlarged head 28 at one end of the bolt that extends along shaft 24 to an opposite end which is selectively threadedly engaged with a nut 30. In one embodiment, shaft 24 may be a threaded shaft for threadedly receiving corresponding nuts, such as selectively removable jam nuts positioned at opposed ends of the shaft. Feedthrough capacitor assembly 20 includes a mounting structure 32 for insulatively carrying feedthrough capacitor 22. Mounting structure 32 includes shaft 24 of bolt 26 that extends through an opening 34 formed in a conductive substrate 36, which mounting structure 32 being removably securable to substrate 36. A tubular conductive member 38 received by shaft 24 also extends through substrate opening 34. A tubular insulator 40 is received over tubular conductive member 38 and also extends through substrate opening 34. As a result, tubular insulator 40 insulatively carries feedthrough capacitor 22.

Figure 3:
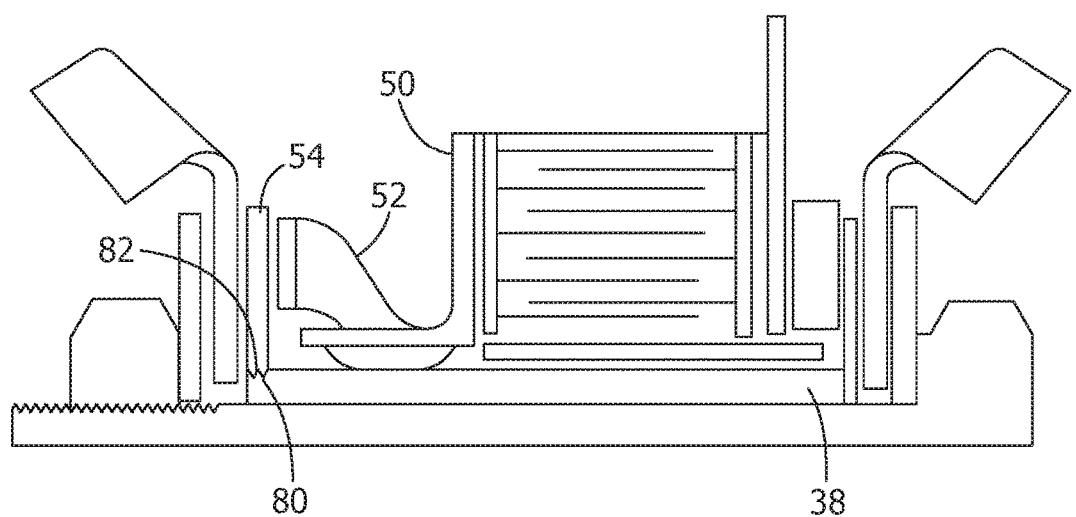
FIG. 3 is a cross section of an exemplary feedthrough capacitor assembly according to the present invention.

As shown in FIG. 2, an exemplary "stack-up" of components are received by shaft 24 of bolt 26. That is, shaft 24 is directed through corresponding openings of these components. For example, a washer 42 such as a steel washer is positioned adjacent head 28 of bolt 26, followed by a ring terminal 44 connected to a circuit (not shown), a washer 46, such as a copper washer, followed by a bushing 48, substrate 36, feedthrough capacitor 22, a neck washer 50, a resilient member 52 such as a wave spring washer which may be composed of a conductive material or an elastomeric material, a washer 54 such as a copper washer, a ring terminal 56 connected to the circuit (not shown), a washer 58 such as a steel washer followed by nut 30. In one embodiment, it may be possible to utilize more washers or less washers than shown in FIG. 2. Upon sufficiently bringing head 28 of bolt 26 toward nut 30 along shaft 24 as a result of threaded actuation toward an installed position 60, this "stack-up" of components are subjected to a clamping force 62 between head 28 and nut 30 for non-movingly securing substrate 36 to conductive member 38. However, for reasons to be discussed in additional detail below, capacitor 22 is not subjected to or only partially subjected to clamping force 62. That is, capacitor 22 is not subjected to the full magnitude of clamping force 62, and, for example, as disclosed for an exemplary embodiment such as shown in FIG. 3, may not be subjected to any of clamping force 62.

As further shown in FIG. 2, tubular conductive member 38 has a length 64, with washers 46, 54 separated by length 64. When subjected to clamping force 62 and compressed as in installed position 60, the collective thicknesses of the components between washer 46 and washer 54, not including the uncompressed thickness of resilient member 52, is less than length 64. That is, the collective thicknesses of bushing 48, substrate 36, feedthrough capacitor 22, and neck washer 50 is less than length 64. The clamping force on the capacitor is controlled by the stiffness and compression of the resilient member or wave spring washer, and the difference between the length of the capacitor and uncompressed wave spring washer stack-up, and tubular conductive member and compressed wave spring washer stack-up. In other words, the amount of compressive force required to compress resilient member 52 to its compressed thickness between washer 54 and neck washer 50 is equal to a reduced amount of clamping force, as compared to clamping force 62, which reduced clamping force is required to maintain feedthrough capacitor 22 (which does not include tubular conductive member 38) in installed position 60. Stated another way, while large clamping forces, such as clamping forces 62 are required for clamping feedthrough capacitor assemblies such as high-power capacitor assemblies (i.e., rated to operate at 50 A or greater) to a substrate, such as a panel, the feedthrough capacitor is subjected to only a reduced portion of clamping force 62 sufficient to secure the feedthrough capacitor in position against the substrate. In an alternate embodiment, such as will be discussed in further detail below, the clamping force that is applied to the feedthrough capacitor is independent of the clamping force applied to the feedthrough capacitor assembly.

As further shown in FIG. 2, as a result of feedthrough capacitor assembly 20 being positioned in installed position 60, there is a conductive path between ring terminal 44 and ring terminal 56 (i.e., from washer 46, which is in physical contact with ring terminal 44, then to tubular conductive member 38, and then to washer 54, which is in physical contact with ring terminal 56). Similarly, as a result of feedthrough capacitor assembly being positioned in installed position 60, there is a high frequency conduction path between ring terminals 44, 56 and conductive substrate 36. The conduction path from ring terminal 44 is as follows: (i.e., from washer 46, which is in physical contact with ring terminal 44, then to tubular conductive member 38, then to a conductive member 65 such as a conductive ring (FIG. 6), then to neck washer 50, and then to feedthrough capacitor 22, which is in physical contact with substrate 36.) The conduction path from ring terminal 56 is as follows: (i.e., from washer 54, which is in physical contact with ring terminal 56, then to tubular conductive member 38, then to a conductive member 65 such as a conductive ring (FIG. 6), also commonly referred to as a crown ring, then to neck washer 50, then to feedthrough capacitor 22, which is in physical contact with substrate 36.) In one embodiment, neck washer 50 includes conductive member 65, which neck washer 50 being carried by tubular conductive member 38. The high-frequency conduction path provides a low resistance, low impedance connection with the independently loaded and positioned feedthrough capacitor.

As shown in FIG. 4, a conductive strip 66 of material has a sufficient length 68 to form conductive member 65 into a ring shape (FIGS. 6, 7) that substantially extends around tubular conductive member 38 (FIG. 2). Conductive strip 66 includes a plurality of parallel slots 70, with each pair of adjacent slots defining a strip 72. As shown in FIG. 5, each strip 72 extends outwardly from opposed ends 75 of a corresponding pair of slots 70 (FIG. 4) to an apex 74 extending a predetermined distance 76 from the surface of strip 66 (FIG. 4), each forming an independent contact and a conductive path between neck washer 50 (FIG. 2) and tubular conductive member 38 (FIG. 2). As shown in FIG. 7, strips 72 are radially inwardly directed, although in one embodiment this arrangement could be reversed such that the strips are radially outwardly directed.

As shown in FIG. 2, washer 54 includes an opening 78 sized to receive shaft 24 of bolt 26, with opening 78 being sufficiently small such that washer 54 abuts an end of tubular conductive member 38 when assembled together. As shown in FIG. 3, which is similar to FIG. 2, washer 54 includes an enlarged opening 80 having a threaded surface 82 for threadedly engaging a corresponding threaded surface formed in tubular conductive member 38, such that washer 54 is selectively movable along axis 25 relative to resilient member 52. As a result of this selective axial positioning of washer 54 relative to an end of resilient member 52 facing neck washer 50, washer 54 acts as a clamping member for compressing resilient member 52 between washer 54 and neck washer 50. The amount of compression applied by washer 54 to resilient member 52 is not only variable or adjustable, but is also independent of the clamping force applied by head 28 of bolt 26 and nut 30.

As shown in FIGS. 2-5, an exemplary method of clamping a feedthrough capacitor 20 to a conductive substrate 36 comprises securing ring terminal 44 or a first electrical lead from an electrical source along shaft 24 of mounting structure 32. Shaft 24 has axis 25 and opposed enlarged ends, such as head 28 and nut 30, or a pair of opposed jamnuts or nuts 30, with at least one of the opposed ends being removed from the shaft to receive ring terminal 44 or the first electrical lead, at least one of the opposed ends being movable along axis 25 relative to another end, the shaft 24 extendable through the substrate opening 34. The method includes inserting the shaft 24 through tubular conductive member 38 received by shaft 24, the tubular conductive member 38 insulatively extendable through the substrate opening 34. The method further includes inserting shaft 24 and tubular conductive member 38 through opening 34 in the conductive substrate 36. The method further includes inserting the tubular conductive member 38 through the capacitor 22. The method further includes securing ring terminal 56 or second electrical lead associated with the electrical source along the shaft 24 of the mounting structure 32. The method further includes securing the removed at least one opposed enlarged end to shaft 24. The method further includes moving the opposed ends along the axis 24 sufficiently toward one another to establish an installed position 60 defining a first conductive path between ring terminal 44 or the first electrical lead, the tubular conductive member 38 and ring terminal 56 or the second electrical lead, and a second conductive path between ring terminal 44 or the first electrical lead, the tubular conductive member 38, the capacitor 22 and the conductive substrate 36. The method further includes wherein upon establishing the installed position 60, the opposed enlarged ends apply a first clamping force 62 for securing the substrate to the tubular conductive member 38, wherein the capacitor 22 is not subjected to the first clamping force 62.

In one embodiment of the method, prior to securing the removed at least one opposed enlarged end of the shaft 24, the method provides inserting tubular conductive member 38 through a resilient member 52, the resilient member applying a second clamping force independent of the first clamping force 62 for securing the capacitor 22 to the conductive substrate 36. In one embodiment of the method, the second clamping force is adjustable.

While the invention has been described with reference to a preferred embodiment, it will be understood by those skilled in the art that various changes may be made and equivalents may be substituted for elements thereof without departing from the spirit and scope of the invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

The invention claimed is:

1. A feedthrough capacitor assembly comprising:
    a film-wound feedthrough capacitor;
    a mounting structure insulatively carrying the capacitor, the structure extendable through an opening in a conductive substrate and removably securable to the substrate, comprising
        a shaft having an axis and opposed enlarged ends, at least one of the opposed ends being removable from the shaft, at least one of the opposed ends being movable along the axis relative to another end, the shaft extendable through the substrate opening; and
        a tubular conductive member received by the shaft, the tubular conductive member extendable through the substrate opening; and in response to insertion of the shaft and the tubular conductive member through the substrate opening and the opposed enlarged ends being sufficiently
        brought toward one another to an installed position, the opposed enlarged ends applying a first clamping force for nonmovingly securing the substrate to the conductive member;
    wherein the capacitor is not subjected to at least a portion of the first clamping force.

2. The feedthrough capacitor assembly of claim 1 further comprising a resilient member exerting a second clamping force independent of the first clamping force for securing the capacitor to the substrate.

3. The feedthrough capacitor assembly of claim 2, wherein the resilient member is a wave spring washer or an elastomeric washer.

4. The feedthrough capacitor assembly of claim 2, further comprising a second conductive member carried by the tubular conductive member and forming a conductive path between the tubular conductive member and the capacitor, the second conductive member positioned between the resilient member and the capacitor.

5. The feedthrough capacitor assembly of claim 4, wherein the second conductive member is a neck washer.

6. The feedthrough capacitor assembly of claim 4, wherein the second conductive member includes a ring forming a conductive path between the tubular conductive member and the capacitor.

7. The feedthrough capacitor assembly of claim 6, wherein the ring is selectively removable from the second conductive member, the ring having multiple independent contacts.

8. The feedthrough capacitor assembly of claim 2, wherein the second clamping force is adjustable.

9. The feedthrough capacitor assembly of claim 8 further comprising a clamping member along the shaft axis, the clamping member selectively positioned a predetermined distance from the capacitor for compressing the resilient member between the clamping member and the capacitor.

10. A feedthrough capacitor assembly comprising
a film-wound feedthrough capacitor;
a mounting structure insulatively carrying the capacitor, the structure extendable through an opening in a conductive substrate and selectably securable to the substrate, the mounting structure comprising
a shaft having an axis and opposed enlarged ends, at least one of the opposed ends being removable from the shaft, at least one of the opposed ends being movable along the axis relative to another end, the shaft extendable through the substrate opening; and
a tubular conductive member received by the shaft, the tubular conductive member extendable through the substrate opening; and
in response to insertion of the shaft and the tubular conductive member through the substrate opening and the opposed enlarged ends being sufficiently brought toward one another to an installed position, the opposed enlarged ends applying a first clamping force for securing the substrate to the tubular conductive member; wherein the capacitor is not subjected to at least a portion of the first clamping force; and
a resilient member exerting a second clamping force independent of the first clamping force for securing the capacitor to the substrate.

11. The feedthrough capacitor assembly of claim 10, wherein the resilient member is a wave spring washer.

12. The feedthrough capacitor assembly of claim 10 further comprising a second conductive member carried by the tubular conductive member and forming a conductive path between the tubular conductive member and the capacitor, the second conductive member positioned between the resilient member and the capacitor.

13. The feedthrough capacitor assembly of claim 12, wherein the second conductive member is a neck washer.

14. The feedthrough capacitor assembly of claim 12, wherein the second conductive member carries a ring forming a conductive path between the tubular conductive member and the capacitor.

15. The feedthrough capacitor assembly claim 14, wherein the ring is selectively removable from the second conductive member.

16. The feedthrough capacitor assembly of claim 10, wherein the second clamping force is adjustable.

17. The feedthrough capacitor assembly of claim 16 further comprising a clamping member movably secured to the tubular conductive member along the shaft axis, the clamping member selectively positioned a predetermined distance from the capacitor for compressing the resilient member between the clamping member and the capacitor.

* * * * *